United States Patent [19]

Levandoski

[11] Patent Number: 4,668,189

[45] Date of Patent: May 26, 1987

[54] METHOD AND APPARATUS FOR ARTICULATING HUMAN AND ANIMAL JAW STRUCTURES

[76] Inventor: Ronald R. Levandoski, 1103 Powell Ave., Erie, Pa. 16505

[21] Appl. No.: 818,677

[22] Filed: Jan. 14, 1986

[51] Int. Cl.⁴ .............................................. A61C 11/00
[52] U.S. Cl. .................................................... 433/55
[58] Field of Search ............................ 433/73, 54, 56

[56] References Cited

U.S. PATENT DOCUMENTS

1,033,562  7/1912  Eltner .................................... 433/56

Primary Examiner—Robert Peshock
Attorney, Agent, or Firm—Charles L. Lovercheck; Wayne L. Lovercheck; Dale R. Lovercheck

[57] ABSTRACT

A dental articulator with two teeth aligning plates is provided. The plates are respectively attached to the upper and lower base means by means of which horizontal, vertical and lateral adjustments of the condylar members can be accomplished independent of one another. The condylar joints are pivoted about a horizontal axis which can be adjusted both laterally and vertically.

19 Claims, 18 Drawing Figures

METHOD AND APPARATUS FOR ARTICULATING HUMAN AND ANIMAL JAW STRUCTURES

REFERENCE TO PRIOR ART

Dental articulators are used to simulate the jaw and jaw hinge mechanism for use in the analysis and diagnosis of dental related problems and creation of various appliances and prostheses and thereby provide according to a patient's particular bite. To accomplish this, upper and lower frame units are generally employed to simulate the upper and lower jaws. Further, condyle ball and socket arrangements are employed in a great many of these devices which were intended to correspond to the actual jaw hinges of humans. Such a device is shown in U.S. Pat. Nos. 3,409,986 to Freeman, 3,478,431 to Depetrio and 3,206,852 to Swanson. To facilitate the description of the present invention, and to promote an understanding of the prior art of articulators in general, the aforementioned patent is referenced in the present description. It will readily appear and be understood by those skilled in the art that the present invention can be incorporated with various other articulators.

U.S. Pat. No. 3,409,986 shows an articulator which permits both angular and vertical adjustments. The upper base member is elevated and supported by pin elements, two of which rest on vertically adjustable platforms. The flexibility of adjustment is not present in this articulator that is present in Applicant's.

The condyle ball and socket joints employed in arcon dental articulators generally provide for significant controlled adjustment to border positions to better reflect actual jaw movements. Consequently, the joints are not interlocking and will not support the upper frame when it is rotated to disengage the false teeth mounted on the articulator. As a result, it has been found useful to provide a secondary mechanism for holding the upper frame on the lower frame when the upper frame is pivoted from the engagement position. Further, the permitted relative lateral displacement of the condyle ball and sockets creates a second operational closed, occludent position when efforts are made to work on the subject teeth with both the upper and lower portions engaged.

There are two general classes of dental articulating instruments, arcon and non-arcon. The arcon articulation concept designates a mechanical feature whereby the anatomy of the jaw joints is reproduced more or less. Condylar spheres are attached to the lower beam and the fossa or condylar housings are attached to the upper beam. In the past, the articulator condyle has been provided with close and intimate contact with the fossa. This was considered necessary in order to guide the instrument to follow adjustable restraints built into the articulator in an attempt to allow reproduction of the various eccentric jaw positions and reliably return models of the jaws to a predetermined "centric" position.

Non-arcon articulators include those which incorporate the condylar spheres on the upper beam and the condylar housings in the lower beam. It has been determined that in most circumstances the arcon and non-arcon articulators produce identical results in the end, but the arcon is considered more easily understood. However, all articulator systems devised have failed to address the fact that in a large percentage of cases there is an unphysiologic relationship between the condyles and fossae which can be corrected or treated by permitting the condyle/fossa spatial relationship to be adjusted. In other words, it may be determined that a particular case may benefit from a decompression of the temporo mandibular joint space. No articulator has yet been devised which offers this possibility.

STATEMENT OF THE INVENTION

This invention relates to an apparatus for articulating models of human or animal jaw structrues for the purpose of orthoenathic surgical diagnosis, fabricating prostheses, fabricating construction bites, analyzing occlusion, and diagnosing and treating temporomandibular joint problems.

OBJECTS OF THE INVENTION

The object of the present invention, the lokus articulator, is to provide a range of adjustment for the decompression and/or repositioning of the condylefossa relationship. This dramatically simplifies diagnosis and treatment especially in cases with problems relating to malpositions or dislocations of the jaw joints.

In addition, the unique capability of this new device to be adjusted in three planes of space for each condyle allows for positive diagnosis and repositioning of patient models for reconstructive or orthoenathic jaw surgery.

With the above and other objects in view, the present invention consists of the combination and arrangement of parts hereinafter more fully described, illustrated in the accompanying drawing and more particularly pointed out in the appended claims, it being understood that changes may be made in the form, size, proportions and minor details of construction without departing from the spirit or sacrificing any of the advantages of the invention.

DETAILED DESCRIPTION OF THE DRAWINGS

Now with more particular reference to the drawings, the articulator 10 comprises the upper frame 11 and the lower frame 12. The upper frame 11 is made up of the upper beam 13 having an upper arm 15 attached thereto and extending forwardly therefrom. An incisal pin 17 is fixed to the forward end of the upper arm 15 and extends downwardly therefrom. The first downwardly extending bracket 20 is fixed to the first end of the upper beam 13 and a second downwardly extending bracket 21 is fixed to the second end of the upper beam 13. A first support or model ring 29, a dental mounting plate is fixed to upper arm 15 and a second support 30, a dental mounting plate is fixed to lower arm 16.

Figures 5, 6, 7:
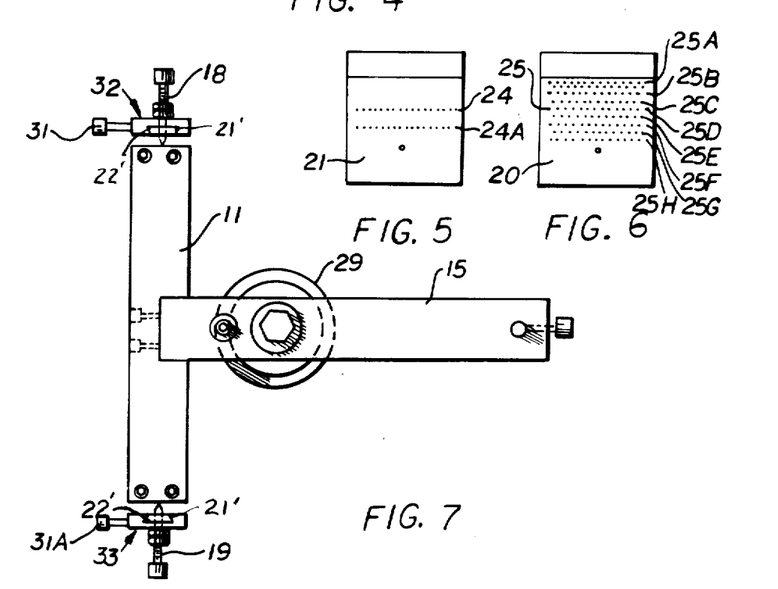
FIG. 5 is an enlarged side view of a part of the articulator.
FIG. 6 is an enlarged partial side view of a part of the articulator.
FIG. 7 is a top view of the articulator.
Figure 8:
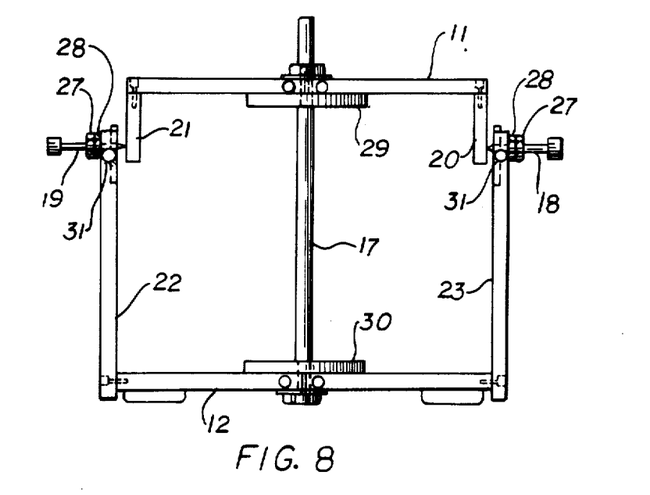
FIG. 8 is a front view of the articulator.
Figure 9:
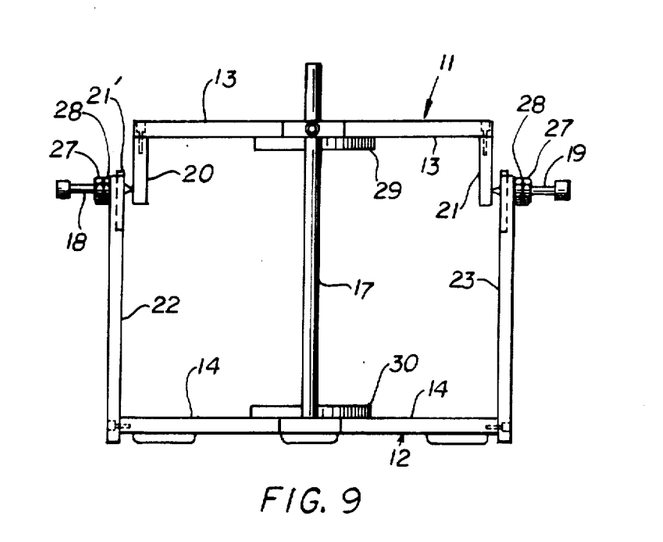
FIG. 9 is a rear view of the articulator.
Figure 10:
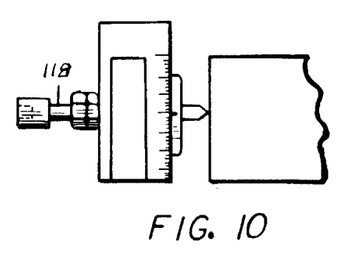
FIG. 10 is an enlarged partial top view of another embodiment of the invention.
Figure 11:
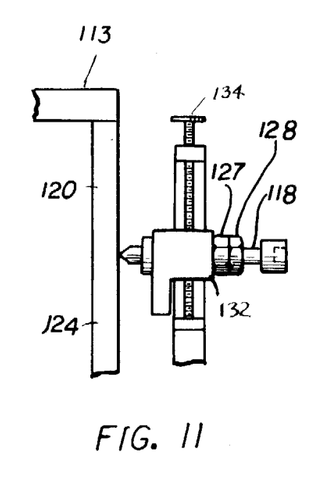
FIG. 11 is an enlarged partial front view of the embodiment of FIG. 10.
Figure 12:
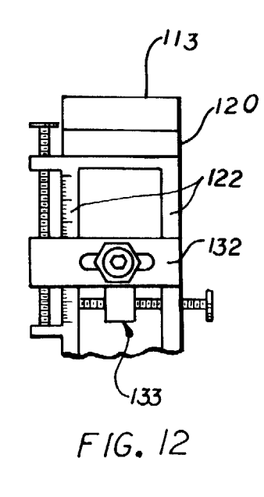
FIG. 12 is an enlarged partial side view of the embodiment of FIGS. 10 and 11.
Figure 13:
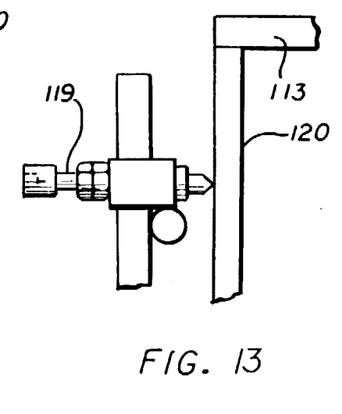
FIG. 13 is an enlarged partial side view of the embodiment of FIGS. 10-12.
Figure 14:
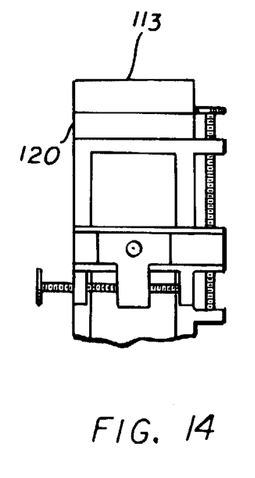
FIG. 14 is an enlarged partial side view of the embodiment of FIGS. 10-13.
Figure 15:
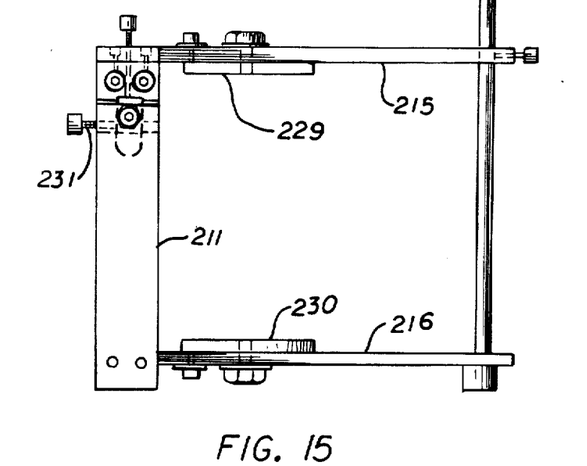
FIG. 15 is a side view of another embodiment of the articulator.
Figure 16:
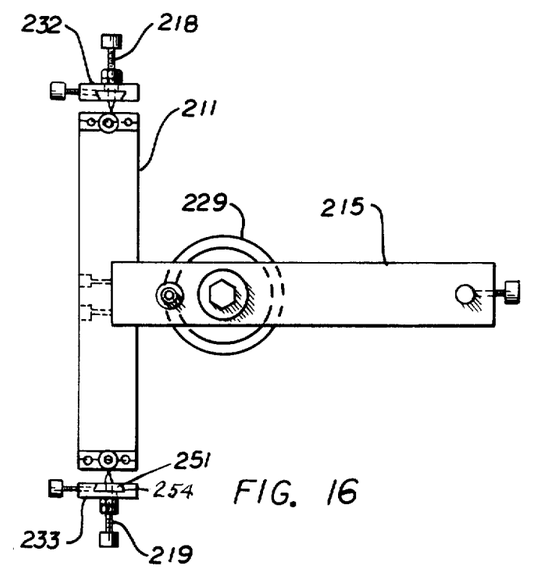
FIG. 16 is a top view of the embodiment of FIG. 15.
Figure 17:
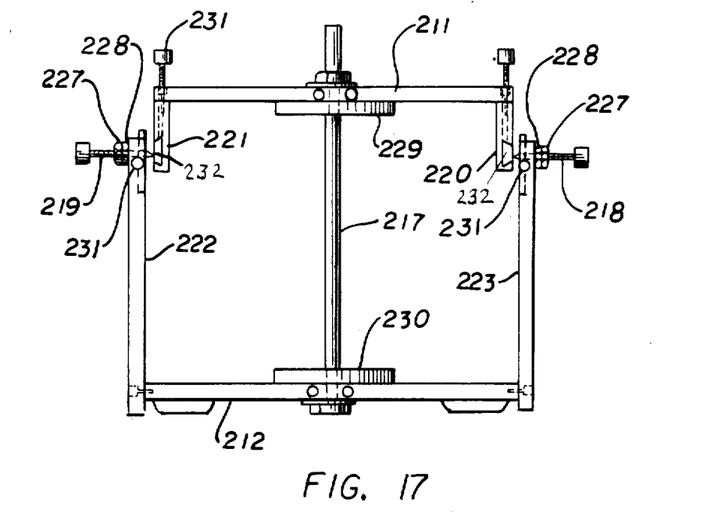
FIG. 17 is a front view of the articulator of FIG. 15.
Figure 18:
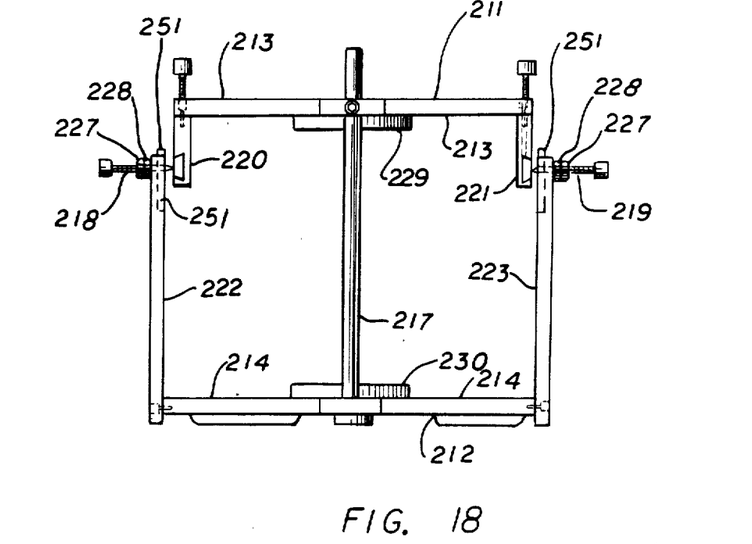
FIG. 18 is a rear view of the articulator shown in FIG. 17.

The lower frame 12 is made up of a laterally extending beam 14 having a first end and a second end and a lower arm 16 is fixed to the lower beam 14 and extends forwardly generally parallel to the upper beam 15. Lower beam 14 has upwardly extending posts 22 and 23 fixed to its ends and slider joints 21' are slidably received in posts 22 and 23. Spaced, preferably conical shaped, orifices 24 are formed in the first downwardly extending bracket 20. In the examples shown, the sliders are dovetail shaped but they could be of different shapes such as T-shaped, cylindrical or square. FIG. 5 shows a downwardly extending bracket 21 with two rows of conical orifices spaced 1 mm apart, the lower orifices staggered to be disposed between the upper row. The two rows are 4 mm apart. FIG. 6 shows a bracket 20 with eight rows with staggered orifices 2 mm apart. The styluses 18 and 19 are threadably received in the dovetail shaped slider 21' which slides vertically in slot 22' which is complementary in shape to the slide. The points of the styluses 18 and 19 are received selectively in the orifices 24, 24A, 25, 25A–25G. The vertical position of the styluses 18 and 19 can be controlled by moving the dovetail shaped slider 21' up or down by loosening the set screws 31 and 31A and allowing the dovetail shaped slider 21' to slide variably in the slots 52. Thus the ends of the upper beam can be individually adjusted horizontally relative to the lower beam by adjusting the styluses 18 and 19 to the desired orifice in the rows of orifices 24 and 25. The beams can also be adjusted vertically to the desired position by adjusting the dovetail shaped slider 21 up or down, and locking it in this position by the set screws 31 and 31A and with the double hex nuts. The adjustment is made to raise the ends of the beam 13 simultaneously or to raise one end relative to the other, to achieve the exact desired position of the styluses 18 and 19 to the support brackets. In addition, the styluses can be adjusted laterally by loosening the double hex nuts and turning one stylus clockwise and the other counter clockwise. This allows the alignment of midlines of mounted models. Loosening of hex screws allows the model ring 29 to be rotated thus allowing rotation only of the maxillary model.

In the embodiment of the invention shown in FIGS. 10 through 14, I show an adjustment for each end of beams 113. Downwardly extending brackets 120 and 121 are provided with adjustments similar to the adjustments on a sight of a rifle. Brackets 120 and 121 have orifices 124, similar to the orifices in brackets 20 and 21 in the embodiment of FIGS. 1–9.

The styluses 118 and 119 are simliar to the stylus 18 shown in the embodiments of FIGS. 1–8 are threadably received in vertical slides 132 and are locked in position by lock nuts 127 and 128 which are similar to the lock nuts 27 and 28. A stylus carrier 132 and 133 replace the sliders 21 of the first embodiment. The horizontal slides 133 are carried on vertical slide 132. Horizontal slide 133 is slidably supported on vertical slide 132 and moves up and down with it. The vertical slide 132 is slidably supported on each upwardly extending post 122.

When the instrument is assembled, each of the points of each of the styluses 118 and 119 engage the selected orifices 124 in the bracket 120. The styluses 118 and 119 may be both adjusted individually to the horizontal plane, the vertical plane and the lateral plane.

In the embodiment of the invention shown in FIGS. 15 through 18, I show an articulator 210 that uses both a vertically slidable dovetail member and a horizontally slidable dovetail member and pivot means for connecting the lower beam to the upper support posts. This embodiment shows an articulator 210 which has styluses 218 and 219, vertical dovetail shaped sliders 251. The styluses 218 and 219 are supported on the dovetail slider members 251 in the slots in the downwardly extending brackets and the points of styluses 218 and 219 engage the horizontal siders 232 provide a pivot means. Each slider and each slot which receives it could be made in any suitable shape.

The upper frame 211 is made up of upper beam 213 having upper arm 215 fixed to it and brackets 220 and 221 fixed to its ends. Lower frame 212 is made up of lower beam 214 with upwardly extending brackets 222 and 223. The first mounting plate 229 is fixed to the upper arm 215 and the second mounting plate 230 is fixed to the lower arm 216. An incisal pin 217 is fixed to the forward end of the arm 215 and extends downwardly therefrom and rests on arm 216. Vertical dovetail shaped slider members 251 are verticaly slidably received in dovetail shaped slots 254 formed in posts 222 and 223. The styluses 218 and 219 are threadably received in dovetail slider member 251. The points of the styluses 218 and 219 engage the horizontally extending horizontal dovetail slider members 232 which may be made of a relatively soft metal, such as aluminum, so that the points of the styluses 218, in effect, when tightened form orifices in the aluminum material slider member 252 which are locked in position by set screw 231. The points of the styluses have a friction fit in the aluminum dovetail slider material when they are tightened. The vertical position of the styluses 218 and 219 can be controlled by moving the vertical slider members 251 up and down by first loosening the set screws 231 and moving the dovetail shaped sliders 251 upwardly or downwardly in the slots 254. The upper beam 211 can be adjusted horizontally by sliding horizontal dovetail members 252 forwardly or rearwardly in slots 253 and can be adjusted horizontally relative to the lower beam by adjusting horizontal dovetail sliders 252 in their slots in brackets 220 and 221. Thus the articulator can be used with universal adjustment and can be readily made.

The instrument is set according to radiographic and gnathologic considerations. A transcranial radiograph of the patient's temporomandibular joints is first obtained. Clinical examination, radiographic evaluation, and past history will determine if the patient requires condylar repositioning or decompression. The transcranial radiograph is then traced on acetate and a point is inserted on the condyle for reference. The corrected condylar position is obtained by superimposing a second condylar tracing in the desired position. The difference in position of the two points can be easily determined, converted into vertical and horizontal components, and the stylus repositioned vertically and horizontally to instantly obtain the same corrected relationship between the upper beam 13 and lower beam 14. This in turn would reposition jaw models previously mounted on the supports in the intercuspal position, to a corrected therapeutic position which would reflect the clinically and radiographically determined repositioning. A cephalometric evaluation can be used to adjust the incisal guide pin for the correct anterior vertical dimension. Thus it is possible to correct each condyle to its appropriate vertical dimension on an individual basis and simultaneously incorporate the ideal anterior vertical dimension. The models of any patient can ben then mounted on this articulator and manipulated at will to any jaw position. This can be done repeatedly, is reproduceable, and the models can be returned to their exact original position with no difficulty. No other device or articulator yet devised allows this ease of adjustment, reproduceability of settings or the potential to adjust for posterior and anterior vertical dimension.

Once the corrected position is obtained and the jaw models are related in a therapeutic position, a compound or wax occlusion record is fabricated by softening the material, placing it between the models, and gently closing the articulator. The cooled record is then transferred to the patient's mouth and he is directed to carefully close into the record. Minor fine tuning adjustments can be accomplished by carefully heating the maxillary occlusal surface and manipulating the patient to close in the desired position. Additional transcranial films are taken to confirm that the condyles are in the desired position and the above procedure is repeated as needed until the desired result is obtained. The articulator is readjusted and the instrument is locked. If the patient is edentulous, the procedure can easily be performed on wax occlusion rims.

Figure 1:
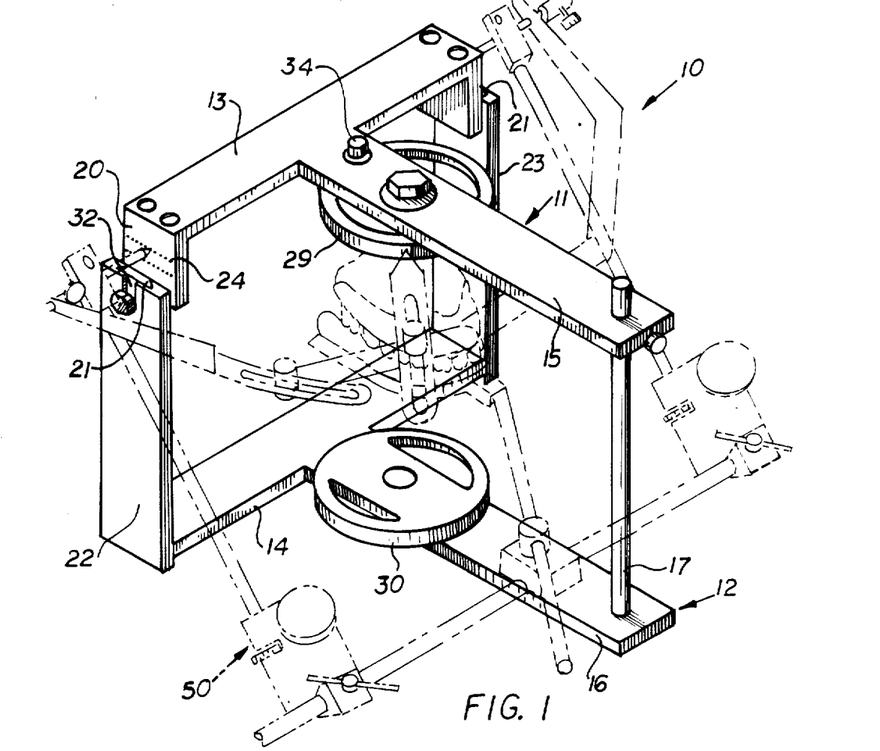
FIG. 1 is an isometric view of the articulator according to the invention with a face bow shown in phantom.
Figure 2:
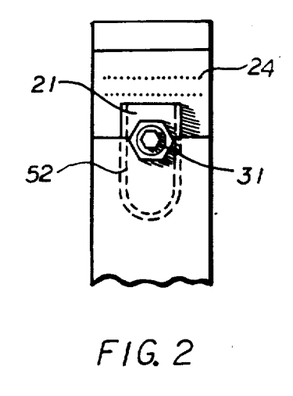
FIG. 2 is an enlarged side view of part of the articulator.
Figure 3:
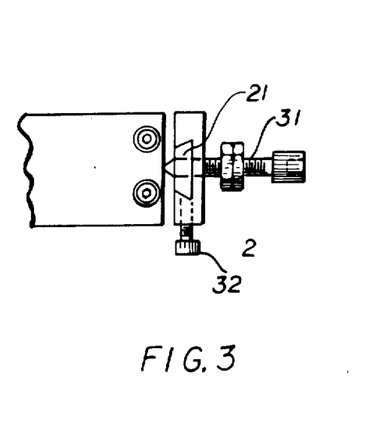
FIG. 3 is an enlarged top view of a part of FIG. 1.
Figure 4:
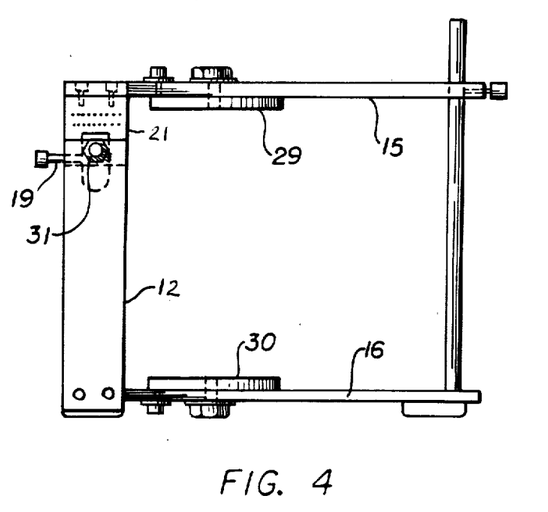
FIG. 4 is a side view of the articulator.

This invention can accept facebow registrations from any major make of facebow, such as the facebow shown in phantom in FIG. 1, and can be adapted to accept any type of mounting rings. It is designed in such a way that the upper model with mounting ring attached can be transferred to another articulator intact. This would require remounting the lower model only, utilizing the therapeutic record. The appliance or prosthesis is then completed on the articulator of choice. In many instances the work can be completed on the lokus articulator.

The foregoing specification sets forth the invention in its preferred, practical forms but the structure shown is capable of modification within a range of equivalents without departing from the invention which is to be understood is broadly novel as is commensurate with the appended claims.

The embodiments of the invention in which an exclusive property or privilege is claimed are defined as follows:

1. A method of articulating dental models providing an articulator comprising a first frame and a second frame,
   pivot means connecting said first frame to said second frame whereby said first frame will swing about an axis relative to said second frame,
   first denture support means on said first frame,
   second denture support means on said second frame,
   said first denture support means and said second denture support means being swingable relative to each other when said first frame is swung about said pivot axis,
   said pivot means comprising two laterally spaced styluses and means fixing said styluses to said second frame,
   said pivot means comprising horizontally adjustable means, vertically adjustable means and lateral adjustable means for adjusting the positions of said styluses on said frame,
   said styluses each having a point engaging a recess means in said first frame and providing transparent sheets,
   (a) determining by clinical examination, radiographic evaluation including a transcranial radiograph and past history whether the patient requires condylar repositioning or decompression.
   (b) tracing an a transparent sheet the condyle and fossa of said transcranial radiograph and determining a point and inserting one said pivot member in said point as a condylar reference,
   (c) determining a corrected condylar position by superimposing a second condylar tracing in a position to give the desired displacement,
   (d) determining the difference in position of the two points and converting them to vertical and horizontal components,
   (e) repositioning the styluses vertically and horizontally to obtain the same relationship between the upper and lower beams of the instrument whereby the models previously mounted on the articulator are repositioned to a corrected therapeutic position which reflects the clinical and radiographically determined position,
   (f) adjusting the threaded styluses to provide a horizontal adjustment in cases where a midline correction is required.

2. The method recited in claim 19 wherein after said articulator is adjusted for condylar correction a compound or wax occlusion record is fabricated by softened material,
   placing the softened material between the models and gently closing the articulator,
   transferring the cooled record to a patient's mouth and directing the patient to carefully close his mouth on the record,
   making fine tuning adjustments by carefully heating the maxillary occlusal surface and manipulating the patient to close in the desired position.

3. The method recited in claim 2 wherein additional transcranial flims are taken to confirm that the condyles are in the desired position and the above procedure is repeated as needed until the desired result is obtained.

4. The method recited in claim 3 wherein the articulator is readjusted to position the models in accordance with the fine tuning adjustments of the instrument recited above and the instrument is locked in position.

5. The method recited in claim 4 wherein the procedure is performed on wax occlusion rims on an edentulous patient.

6. The method recited in claim 5 wherein a facebow registration is supported on said instrument whereby the upper model is supported on a mounting ring whereby the upper model can be transferred to another articulator.

7. An articulator comprising a first frame and a second frame,
- pivot means connecting said first frame to said second frame whereby said first frame will swing about an axis relative to said second frame,
- first denture support means on said first frame,
- second denture support means on said second frame,
- said first denture support means and said second denture support means being swingable relative to each other when said first frame is swung about said pivot axis,
- said pivot means comprising horizontally adjustable means and vertically adjustable means,
- said pivot means comprising two spaced styluses and means fixing said styluses to said second frame,
- said styluses each having a point engaging a recess means in said first frame providing said pivot means,
- said stylus means comprising a threaded member threadably received in said adjustable means in said second frame,
- said vertically adjustable means comprising a vertically extending first slot in said second frame,
- a first slider complementary in shape to said vertically extending slot,
- said stylus means being threadably received in said first slider,
- means to lock said first slider in position in said first slot.

8. The articulator recited in claim 7 wherein said means to lock said styluse in position comprises a second slot in said second frame communicating with said first slot,
- said stylus means extends through said second slot.

9. The articulator recited in claim 8 wherein said orifice means in said first frame comprises vertically and horizontally spaced rows of orifices in said first frame adapted to selectively receive said point of said stylus means whereby said second denture support means can be adjusted laterally and vertically relative to said second denture support means.

10. The articulator recited in claim 8 wherein said horizontally adjustable means comprises a horizontally slidable stylus means horizontally slidable relative to said second frame,
- a vertically slidable stylus support supporting said horizontally slidable stylus means vertically slidable relative to said second support means,
- first threaded means for said vertical means on said first horizontally slidable means,
- second threaded means slidable means for moving said horizontally slidable means relative to said frame whereby said styluses can be moved both vertically and horizontally to adjust the position of said styluses.

11. The articulator recited in claim 8 wherein said horizontally adjustable means comprises a third slot disposed in said first frame,
- second slider complementary in shape disposed in said third slot,
- said orifice means being disposed in said second slider 12. The articulator recited in claim 7 wherein said horizontal adjusting means comprises a horizontal slider supported in a horizontal slot in said second frame,
- said recess means engaging said recess in said horizontal slider.

13. The articulator recited in claim 7 wherein said vertically and horizontally slidable members are supported on said posts,
- threaded member actuable by slidable threaded means on posts pivotally engaging said slidable members for adjusting said styluses horizontally,
- and second threaded means on said slidable members for adjusting said sytluses vertically.

14. The articulator recited in claim 11 wherein said first threaded member engages slidable threaded means supported on said first post,
- said second threaded member actuable by said second threaded member being fixed to said second bracket to be selectively received in said orifices in said first bracket whereby said second frame can be adjusted to swing about a selected axisrelative to said first frame.

15. The articulator recited in claim 12 wherein said first threaded members are supported on said posts by means of vertically spaced lugs,
- said vertical sliding means has a threaded lug thereon,
- said first threaded member threadably engages said first threaded lug on said vertical slidable member whereby said vertical slidable member can be adjusted vertically on said post.

16. The articulator recited in claim 13 wherein spaced lugs are provided on said vertical slidable member,
- a threaded lug supported on said horizontal slidable member,
- said second threaded member is supported by said spaced lugs on said vertical sliding member and threadably engages said lug on said horizontal slidable member whereby said horizontal slidable member can be adjusted horizontally relative to said vertical slidable member.

17. A method of articulating dental models for a patient providing an articulator comprising a first frame and a second frame,
- pivot means connecting said first frame to said second frame whereby said first frame will swing about an axis relative to said second frame,
- first denture support means on said first frame,
- second denture support means on said second frame,
- said first denture support means and said second denture support means being swingable relative to each other when said first frame is swung about said axis,
- adjusting means for adjusting said pivot means vertically and horizontally, whereby said first denture support means and said second denture support means can be adjusted relative to one another,
- said method comprising,
  - (a) determining whether a patient needs condylar repositioning,
  - (b) mounting first dentures on said first denture support and second dentures on said second denture support in the cuspal position,
  - (c) providing a first condylar facsimile and fossa of the patient,
  - (d) determining the magnitude of correction necessary to provide therapeutic condylar joint space, by providing a second condylar facsimile of said first mentioned condyle and superimposing said second condylar facsimile over said first mentioned condylar facsimile and shifting said facsimiles relative to one another by the amount of the correction necessary, (e) determining the magnitude of a horizontal component and a vertical component of the correction, (f) adjusting the pivot means vertically and horizontally a distance equal to said horizontal component and said vertical component respectively to obtain the same relationship between the upper and lower beams of the articulator whereby the models previously mounted on the articulator are repositioned to a corrected position.

18. The method recited in claim 17 wherein said pivot means comprises styluses and means cooperating with said styluses to provide said adjustment.

19. The method recited in claim 17 wherein said adjusting means comprises threaded styluses to provide a horizontal adjustment in cases where a midline correction is required.

* * * * *